(12) United States Patent
Durrant et al.

(10) Patent No.: US 7,879,891 B2
(45) Date of Patent: Feb. 1, 2011

(54) CASPASE INHIBITOR PRODRUGS

(75) Inventors: Steven Durrant, Abingdon (GB); Jean-Damien Charrier, Wantage (GB); John Studley, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 994 days.

(21) Appl. No.: 11/489,939

(22) Filed: Jul. 20, 2006

(65) Prior Publication Data

US 2007/0155718 A1    Jul. 5, 2007

Related U.S. Application Data

(60) Provisional application No. 60/703,375, filed on Jul. 28, 2005.

(51) Int. Cl.
*C07D 498/14* (2006.01)
*A61K 31/4725* (2006.01)
*A61K 31/4439* (2006.01)
*A61K 31/424* (2006.01)

(52) U.S. Cl. .................. 514/375; 514/338; 514/309; 546/141; 546/271.7; 548/218

(58) Field of Classification Search .......... 548/217, 548/218
See application file for complete search history.

(56) References Cited

U.S. PATENT DOCUMENTS

| | | | |
|---|---|---|---|
| 5,672,584 A * | 9/1997 | Borchardt et al. ........... 514/11 |
| 6,184,210 B1 | 2/2001 | Keana et al. |
| 6,184,244 B1 | 2/2001 | Karanewsky et al. |
| 6,187,771 B1 | 2/2001 | Karanewsky et al. |
| 6,197,750 B1 | 3/2001 | Karanewsky et al. |
| 6,242,422 B1 | 6/2001 | Karanewsky et al. |
| 6,531,474 B1 | 3/2003 | Wannamaker et al. |
| 6,632,962 B2 | 10/2003 | Golec et al. |
| 6,689,784 B2 | 2/2004 | Bebbington et al. |
| 6,800,619 B2 | 10/2004 | Charrier et al. |
| 7,053,057 B2 | 5/2006 | Golec et al. |
| 7,109,357 B2 | 9/2006 | Wannamaker et al. |
| 7,205,327 B2 | 4/2007 | Kay et al. |
| 2002/0045623 A1 | 4/2002 | Charrier et al. |
| 2003/0092703 A1 | 5/2003 | Mortimore et al. |
| 2003/0232846 A1 | 12/2003 | Golec et al. |
| 2004/0072850 A1 | 4/2004 | Knegtel et al. |
| 2004/0242494 A1 * | 12/2004 | Brenchley et al. ........... 514/19 |

FOREIGN PATENT DOCUMENTS

| WO | 99/46248 A1 | 9/1999 |
|---|---|---|
| WO | 00/01666 A1 | 1/2000 |
| WO | 01/05772 A1 | 1/2001 |
| WO | 02/085899 A1 | 10/2002 |

OTHER PUBLICATIONS

Lepschy et al. Liebigs Ann. Chem. 1974, 1753-1762.*
Linton S D et al: "Acyl Dipeptides as Reversible Caspase Inhibitors, Part 1: Initial Lead Optimization" Bioorganic & Medicinal Chemistry Letters, 12 (2002) 2969-2971.
Linton S D et al: "Acyl Dipeptides as Reversible Caspase Inhibitors, Part 2: Further Optimization" Bioorganic & Medicinal Chemistry Letters, 12 (2002) 2973-2975.

* cited by examiner

*Primary Examiner*—Rebecca L Anderson
*Assistant Examiner*—Matthew P Coughlin
(74) *Attorney, Agent, or Firm*—Jennifer G. Che

(57) ABSTRACT

This invention relates to prodrugs of caspase inhibitors comprising of a furo[3,2-d]oxazolin-5-one moiety which, under specific conditions, can convert into biologically active compounds, particularly caspase inhibitors.

This invention also relates to the processes for preparing these prodrugs of caspase inhibitors.

This invention further relates to pharmaceutical compositions comprising said prodrugs and to the use thereof for the treatment of diseases related to inflammatory or degenerative conditions.

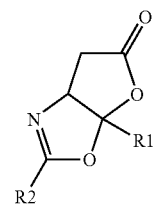

18 Claims, No Drawings

CASPASE INHIBITOR PRODRUGS

CROSS REFERENCE TO RELATED APPLICATIONS

This present application claims the benefit, under 35 U.S.C. §119, to U.S. Provisional Application No. 60/703,375 filed Jul. 28, 2005; the entire disclosure of which is incorporated herein by reference.

FIELD OF THE INVENTION

This invention relates to prodrugs of caspase inhibitors comprising of a furo[3,2-d]oxazolin-5-one moiety which, under specific conditions, convert into biologically active compounds, particularly caspase inhibitors, and wherein the prodrugs have formula I, and $R^1$ and $R^2$ are as defined below.

This invention also relates to the processes for preparing these prodrugs of caspase inhibitors.

This invention further relates to pharmaceutical compositions comprising said prodrugs and to the use thereof for the treatment of diseases related to inflammatory or degenerative conditions.

BACKGROUND OF THE INVENTION

Caspases are a family of cysteine protease enzymes that are key mediators in the signaling pathways for apoptosis and cell disassembly. The utility of caspase inhibitors to treat a variety of mammalian disease states associated with an increase in cellular apoptosis has been demonstrated using peptidic caspase inhibitors. These inhibitors are useful for reducing infarct size and inhibiting cardiomyocyte apoptosis after myocardial infarction, reducing lesion volume and neurological deficit resulting from stroke, reducing post-traumatic apoptosis and neurological deficit in traumatic brain injury, treating fulminant liver destruction, and improving survival after endotoxic shock.

The use of prodrugs imparts desired characteristics such as increased bioavailability or increased site-specificity for known drugs. Accordingly, there is a need for prodrugs of caspase inhibitors.

SUMMARY OF THE INVENTION

Compounds of this invention, and pharmaceutically acceptable compositions thereof, are effective as prodrugs of caspase inhibitors. In certain embodiments, these prodrugs comprise of a furo[3,2-d]oxazolin-5-one moiety which, under specific conditions, convert into biologically active compounds, particularly caspase inhibitors. These prodrugs have formula I, or a pharmaceutically acceptable salt thereof, wherein and $R^1$ and $R^2$ are as defined below.

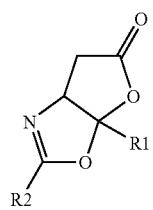

Formula I

These compounds, and pharmaceutically acceptable compositions thereof, are useful for treating a variety of mammalian disease states associated with an increase in cellular apoptosis, including, but not limited to, myocardial infarction, stroke, traumatic brain injury, fulminant liver destruction, endotoxic shock, sepsis, septic shock, chronic hepatitis, and pancreatitis.

DETAILED DESCRIPTION OF THE INVENTION

This invention provides compounds of Formula I:

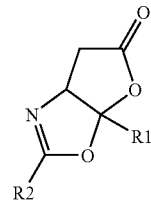

Formula I wherein $R^1$ is H, $R^4$, haloalkyl, $CHN_2$, $CH_2Cl$, $CH_2F$, —$CH_2OPO(R^4)_2$, —$CH_2OPO(OR^4)_2$, or —$C_{1-2}$alkyl-$R^3$—$R^4$;

$R^2$ is a $P_4$—$P_3$—$P_2$, $P_3$—$P_2$, or $P_2$ moiety of a caspase inhibitor;

$R^3$ is —O—, —NH—, —$NR^4$—, —S—, or —O(C=O)—;

$R^4$ is $C_{1-12}$ aliphatic, $C_{6-10}$ aryl, 5-10 membered heterocyclyl, 5-10 membered heteroaryl, $C_{3-10}$cycloaliphatic, —($C_{1-6}$alkyl)-$C_{6-10}$aryl, —($C_{1-6}$alkyl)-(5-10 membered heteroaryl), —($C_{1-6}$alkyl)-(5-10 membered heterocyclyl), or —($C_{1-6}$alkyl)-$C_{3-10}$cycloaliphatic; wherein said $R^4$ group is optionally substituted with 0-5 J and 0-2 $J^2$;

or two $R^4$ groups, together with the atom to which they are attached, form a 3-8 membered monocyclic or 8-12 membered bicyclic ring optionally substituted with 0-5 J and 0-2 $J^2$;

J is halogen, —OR', —$NO_2$, —CN, —$CF_3$, —$OCF_3$, —R', 1,2-methylenedioxy, 1,2-ethylenedioxy, —N(R')$_2$, —SR', —SOR', —$SO_2R'$, —$SO_2N(R')_2$, —$SO_3R'$, —C(O)R', —C(O)C(O)R', —C(O)C(O)OR', —C(O)C(O)N(R')$_2$, —C(O)CH$_2$C(O)R', —C(S)R', —C(S)OR', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NR')N(R')$_2$, —C(O)N(OR')R', —C(=NOR')R', —OP(O)(OR')$_2$, —P(O)(R')$_2$, —P(O)(OR')$_2$, or —P(O)(H)(OR');

$J^2$ is =NR', =N(OR'), =O, or =S;

R' is H, $C_{1-12}$ aliphatic, $C_{6-10}$ aryl, 5-10 membered heterocyclyl, 5-10 membered heteroaryl, $C_{3-10}$cycloaliphatic, —($C_{1-6}$alkyl)-$C_{6-10}$aryl, —($C_{1-6}$alkyl)-(5-10 membered heteroaryl), —($C_{1-6}$alkyl)-(5-10 membered heterocyclyl), or —($C_{1-6}$alkyl)-$C_{3-10}$cycloaliphatic;

each R' is independently and optionally substituted with 0-5 occurrences of H, $C_{1-6}$alkyl, $CF_3$, halogen, $NO_2$, $OCF_3$, CN, OH, O($C_{1-6}$alkyl), $NH_2$, N($C_{1-6}$alkyl), N($C_{1-6}$alkyl)$_2$, C(=O)CH$_3$, or $C_{1-6}$alkyl optionally interrupted 1 time with a heteroatom selected from O, N, and S; wherein each $C_{1-6}$alkyl is unsubstituted;

unless otherwise indicated, any group with suitable valence is optionally substituted with 0-5 J and 0-2 $J^2$.

As used herein, a specified number range of atoms includes any integer therein. For example, a group having from 1-4 atoms could have 1, 2, 3, or 4 atoms.

As used herein, an aliphatic group is a straight-chained, branched, or cyclic hydrocarbon group that is completely saturated or partially saturated with 1 or more units of unsaturation. Unless otherwise specified, the aliphatic group has from 1 to 12 carbon atoms. As would be understood, alkenyl and/or alkynyl aliphatic groups have a minimum of 2 carbon atoms. Preferred aliphatic groups are alkyl groups (preferably having from 1 to 6 atoms).

"Cycloalkyl", "cycloalkenyl", and "cycloaliphatic" groups have between 3 and 10 carbon atoms and are monocyclic or bicyclic, fully saturated or partially unsaturated, linearly fused, bridged, or spirocyclic.

As used herein, "aromatic group" or "aryl" refers to a 6-14-membered ring system that contains at least one aromatic (i.e. fully unsaturated) ring. Examples of aromatic rings include, but are not limited to, phenyl, naphthyl, benzimidazole, and benzodioxane.

As used herein a "heteroaryl" refers to a ring system having 5-14 members and 1, 2, or 3 heteroatoms independently selected from N, NR', O, S, SO, and $SO_2$, wherein at least one ring is heteroaromatic (a fully unsaturated ring containing up to 4 heteroatoms selected from O, N, an S; e.g., pyridyl, thiophene, or thiazole).

As used herein a "heterocycle" refers to ring system having 3-10 members and 1, 2, or 3 heteroatoms independently selected from N, NR', O, S, SO, and $SO_2$, wherein no ring is aromatic (e.g., piperidine and morpholine).

Further examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

Further examples of heterocyclic rings include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR'—, —O—, —S—, —$CO_2$—, —OC(O)—, —C(O) CO—, —C(O)—, —C(O)NR'—, —C(=N—CN), —NR'CO—, —NR'C(O)O—, —$SO_2$NR'—, —NR'$SO_2$—, —NR'C(O)NR—, —OC(O)NR'—, —NR'$SO_2$NR—, —SO—, or —$SO_2$—, wherein R' is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —$CH_2CH_2CH_3$ were optionally interrupted with —O—, the resulting compound could be —$OCH_2CH_3$, —$CH_2OCH_3$, or —$CH_2CH_2OH$.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

Each of the above aliphatic, aryl, cycloaliphatic, heteroaryl, and heterocyclyl may be optionally substituted with appropriate substituents (preferably up to 5, more preferable up to 3, and even more preferably, 0 or 1).

As described herein, "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position.

Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

Unless otherwise indicated, preferred substituents on an aliphatic, aryl, cycloaliphatic, heteroaryl, or heterocyclyl are selected from halogen, —OR', —$NO_2$, —$CF_3$, —$OCF_3$, —R', oxo, —OR', —O-benzyl, —O-phenyl, 1,2-methylenedioxy, 1,2-ethylenedioxy, —N(R')$_2$, —C(O)R', —COOR' and —CON(R')$_2$, wherein R' is defined herein (and is preferably H, C$_{1-6}$alkyl, C$_{2-6}$alkenyl, or C$_{2-6}$alkynyl, with C$_{1-6}$alkyl being most preferred). It should be understood that this definition would include a perfluorinated alkyl group.

In certain embodiments of this invention, preferred substituents on a nitrogen atom are selected from the group consisting of —R$^7$, —SOR$^7$, —SO$_2$R$^7$, —SO$_2$N(R$^7$)$_2$, —SO$_3$R$^7$, —C(O)R$^7$, —C(O)C(O)R$^7$, —C(O)C(O)OR$^7$, —C(O)C(O)N(R$^7$)$_2$, —C(O)CH$_2$C(O)R$^7$, —C(O)OR$^7$, —C(O)N(R$^7$)$_2$, —C(S)N(R$^7$)$_2$, —(CH$_2$)$_{0-2}$NHC(O)R$^7$, —C(=NR$^7$)N(R$^7$)$_2$, —C(O)N(OR$^7$)R$^7$, —C(=NOR$^7$)R$^7$, —P(O)(R$^7$)$_2$, —P(O)(OR$^7$)$_2$, and —P(O)(H)(OR$^7$), wherein R$^7$ is defined herein.

In other embodiments the nitrogen substituents are H, —R$^7$, COR$^7$, S(O)$_2$R$^7$, or CO$_2$R$^7$. In yet other embodiments, the nitrogen substituents are —R$^7$ or —C(O)R$^7$.

It will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise indicated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{17}$C-enriched carbon are within the scope of this invention.

The compounds of this invention may be obtained by any method, including general, synthetic methods known to those skilled in the art for analogous compounds. For the purposes of illustration, the following scheme for the synthesis of the compounds of the present invention is provided.

The following abbreviations are used:
TFAA—trifluoroacetic anhydride
EDC—1-ethyl-3-(3-dimethyl aminopropyl)-carbodiimide
DCM—dichloromethane
$^1$HNMR—Proton Nuclear Magnetic Resonance
$^{19}$FNMR—Fluorine Nuclear Magnetic Resonance
$^{13}$C NMR—Carbon Nuclear Magnetic Resonance
LCMS—liquid chromatography/mass spectroscopy Scheme I formula II → (CF$_3$CO)$_2$O / DCM → formula I Scheme I depicts formation of compounds of formula I. Compounds of formula I can be prepared by treatment of a compound of formula II using a carboxylic acid activating agent and a suitable solvent, such as DCM (dichloromethane). Examples of carboxylic acid activating agents include, but are not limited to, TFAA, acetic anhydride, EDC, and carboxylic anhydrides. It will be apparent to those skilled in the art that TFAA can be replaced by any reagent used to activate carboxylic acids. It will also be apparent for those skilled in the art that DCM can be replaced by other suitable organic solvents.

As would be realized by skilled practitioners, certain process steps may be accomplished in discrete steps or in situ. For example, if a process of this invention involves deprotection and subsequent reaction of an amine, these steps may be accomplished in a step-wise or in a one step procedure.

Chiral aspartic acid residues, such as certain compounds of formula II, form enantiomerically pure products when subject to the conditions described in Scheme I. Racemic aspartic acid residues, such as certain other compounds of formula II, form a mixture of syn isomers.

In certain embodiments, the above processes are as described herein (e.g., in the schemes, examples, and accompanying description).

One embodiment provides a process of preparing a compound of formula I

I wherein R$^1$ and R$^2$ are as defined herein;

comprising treating a compound of formula II:

II wherein R$^1$ and R$^2$ are as defined herein;

with a carboxylic acid activating agent and a suitable solvent to form a compound of formula I. In some embodiments, the carboxylic acid activating agent is selected from TFAA, acetic anhydride, or EDC. In some embodiments, the carboxylic acid activating agent is TFAA.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

For example, a carboxylic acid group in a compound of this invention may be derivatized as, for example, an ester. Preferred esters would be those derived from:

a C$_{1-6}$ straight-chained or branched alkyl, alkenyl, or alkynyl, wherein the alkyl, alkenyl, or alkynyl is optionally substituted with C$_{6-10}$aryl, CF$_3$, Cl, F, OMe, OEt, OCF$_3$, CN, or NMe$_2$;

a $C_{1-6}$ cycloalkyl, wherein 1-2 carbon atoms in the cycloalkyl is optionally replaced with —O— or —$NR^9$—.

Compounds of this invention having a carbonyl group may be similarly derivatized as, e.g., an acetal, ketal, oxime (=$NOR^9$), hydrazine (=$NN(R^9)_2$), thioacetal, or thioketal.

Appropriate derivatives of amines are known in the art and are also included within the scope of this invention.

Certain of the above derivatives would include the protective groups known to skilled practitioners (see, e.g., T. W. Greene & P. G. M Wutz, "Protective Groups in Organic Synthesis", $3^{rd}$ Edition, John Wiley & Sons, Inc. (1999)). As would be recognized by a skilled practitioner, these protective groups may also be employed in the processes of this invention.

The compounds of this invention may be assayed for their ability to inhibit apoptosis, the release of IL-1β or caspase activity directly. Assays for each of the activities are known in the art. However, as would be recognized by a skilled practitioner, a prodrug compound of this invention should be active only in assays where the prodrug moiety would be cleaved, typically in in vivo assays.

Compounds of this invention may be tested in assays such as those described in WO 99/47545 and WO 2004/106304, the contents of which are hereby incorporated by reference.

Portions of $R^2$ are specifically referred to in the art as a $P_2$, $P_3$ or $P_4$ moiety or site. These $P_x$ terms are references to the amino acid sequence next to the aspartyl cleavage site of a particular caspase substrate. $P_1$ refers to the aspartyl residue of the substrate where caspase-induced cleavage occurs in the natural substrate. In the design of new, nonpeptidic caspase inhibitors, the $P_x$ designation is often retained to show which portion of the amino acid sequence has been replaced by the non-peptidic moiety. As used herein, the term "$P_4$—$P_3$—$P_2$", "$P_3$—$P_2$", or "or $P_2$" moiety refers to either the amino acid sequence described above or a chemical moiety known to replace such a sequence for the purpose of being a caspase substrate.

Examples of $P_4$—$P_3$—$P_2$, $P_3$—$P_2$, or $P_2$ moieties that are non-peptidic are described in U.S. Pat. No. 5,919,790 (Allen et al.); U.S. Pat. No. 5,874,424 (Batchelor et al.); U.S. Pat. No. 5,847,135 (Bemis et al.); U.S. Pat. No. 5,843,904 (Bemis et al.); U.S. Pat. No. 5,756,466 (Bemis et al.); U.S. Pat. No. 5,716,929 (Bemis et al.); U.S. Pat. No. 5,656,627(Bemis et al.); WO 99/36426 (Warner-Lambert); Dolle et al., *J. Med. Chem.*, 40, 1941 (1997); WO 98/10778 (Idun); WO 98/11109 (Idun); WO 98/11129 (Idun) and WO 98/16502 (Warner Lambert), all of which are incorporated by reference.

According to one embodiment of this invention, the $P_4$—$P_3$—$P_2$, $P_3$—$P_2$, or $P_2$ moiety of a caspase inhibitor is an optionally substituted group selected from $C_{6-10}$ aryl, 5-10 membered heteroaryl, and one of the scaffolds shown in Table 1:

TABLE 1

$P_4$—$P_3$—$P_2$—, $P_3$—$P_2$, or $P_2$ Groups

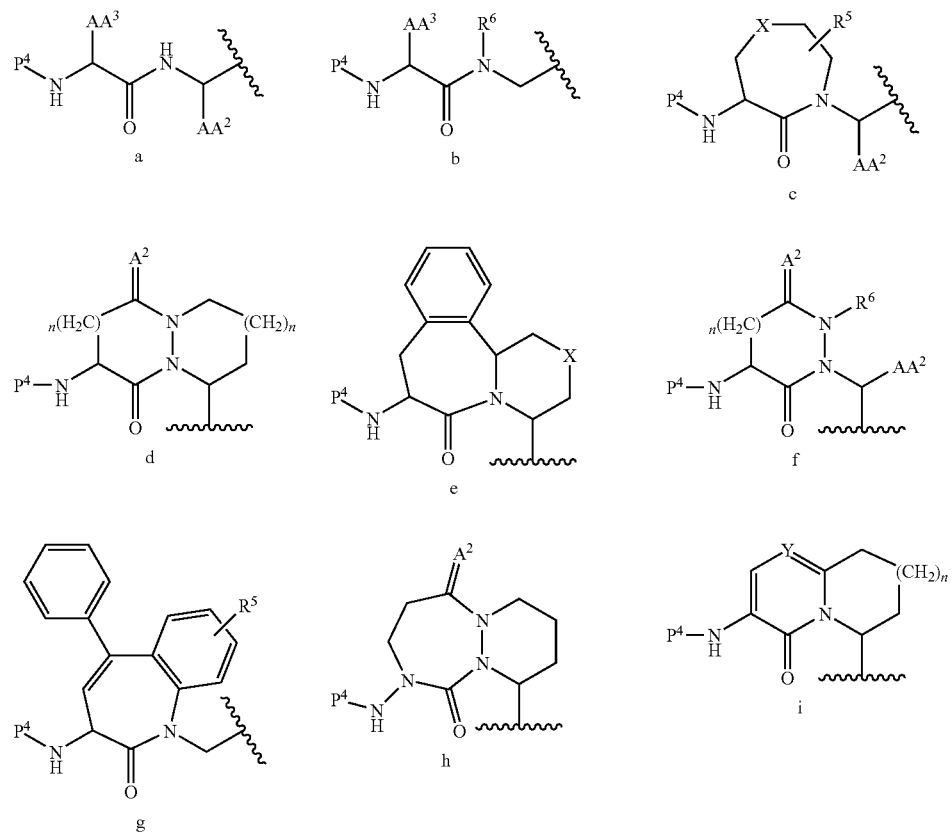

TABLE 1-continued
P$_4$—P$_3$—P$_2$—, P$_3$—P$_2$, or P$_2$ Groups
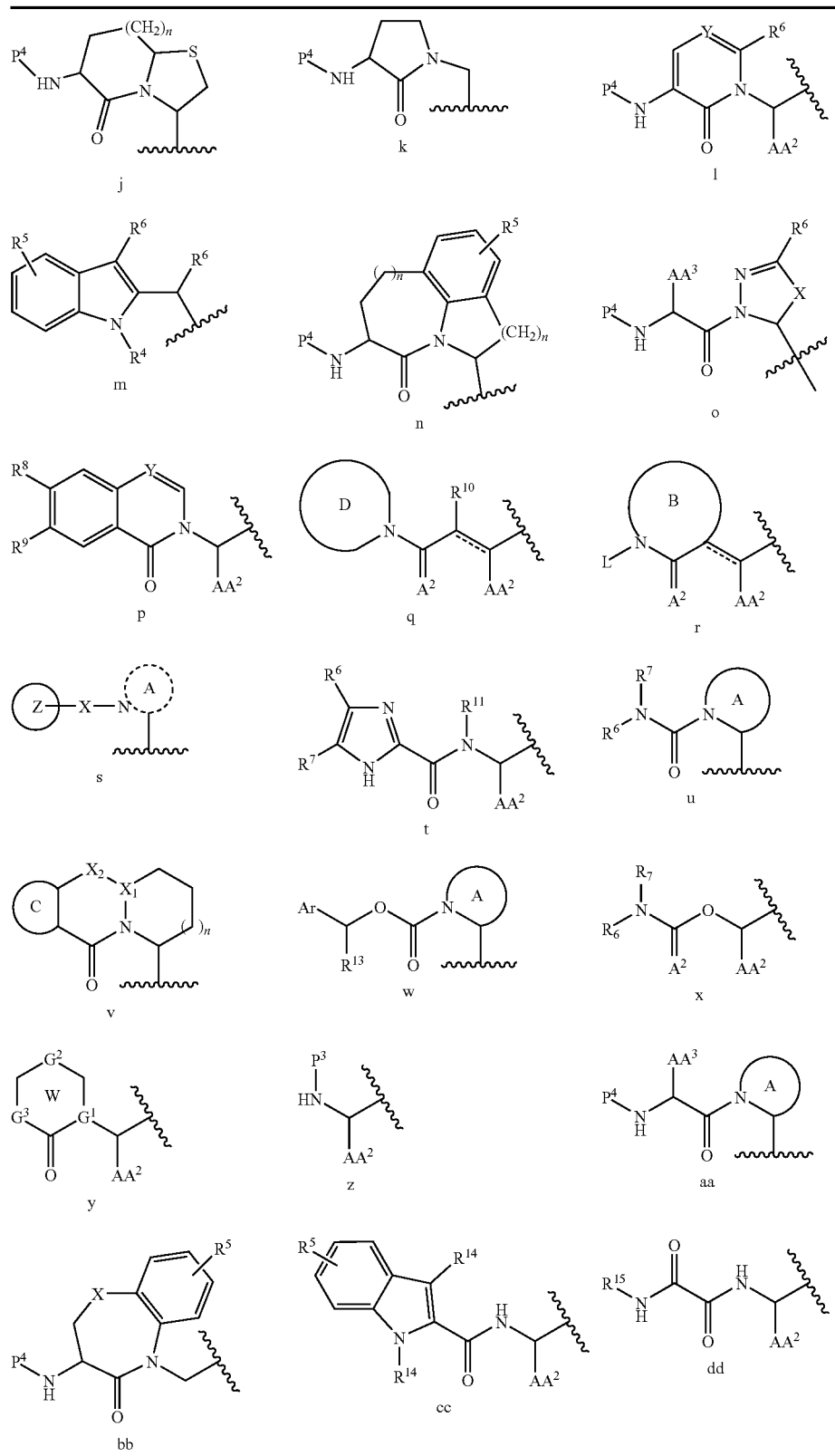

wherein n is 0-3;

each $P^3$ and $P^4$ is independently -(T)$_p$-R;

T is —CO—, —C(O)O—, —C(O)C(O)O—, —C(O)NR$^7$—, —C(O)NR$^7$NR$^7$—, —C(O)C(O)NR$^7$—, —SO$_2$NR$^7$—, or —SO$_2$—;

p is 0 or 1;

R is H, $C_{1-12}$ aliphatic, $C_{6-10}$ aryl, 5-10 membered heterocyclyl, 5-10 membered heteroaryl, $C_{3-10}$cycloaliphatic, —($C_{1-6}$alkyl)-$C_{6-10}$aryl, —($C_{1-6}$alkyl)-(5-10 membered heteroaryl), —($C_{1-6}$alkyl)-(5-10 membered heterocyclyl), —($C_{1-6}$alkyl)-benzo($C_{3-10}$cycloalkyl) or —($C_{1-6}$alkyl)-$C_{3-10}$cycloaliphatic;

each AA, $AA^2$, and $AA^3$ is independently an amino acid side chain;

X is —N—, —O—, —S—, —SO—, —SO$_2$—, —CHF—, —CF$_2$—, —C(R$^{11}$)$_2$—, —C=O—, or —C=NOR$^{11}$—;

$X_2$—$X_1$ is —N(R$^{11}$)—C(R$^{11}$)—, —C(R$^{11}$)$_2$—C(R$^{11}$)—, —C(R$^{11}$)$_2$—N—, —N=C—, —C(R$^{11}$)=N—, —C(R$^{11}$)=C—, —C(=O)—N—, or —C(=O)—C(R$^{11}$)—;

$A^2$ is O, S, or H$_2$;

Y is N or CR$^8$;

Ar is optionally substituted $C_{6-10}$ aryl or optionally substituted 5-10 membered heteroaryl;

L is R$^7$, (CH$_2$)$_n$R$^7$, COR$^7$, CO$_2$R$^7$, SO$_2$R$^7$, CON(R$^7$)$_2$, or SO$_2$N(R$^7$)$_2$;

$G^1$ and $G^3$ are independently selected from N or C;

$G^2$ is a valence bond, O, S, N, or C;

Ring W contains 0-2 double bonds and is optionally fused to a saturated or unsaturated 5-7 membered ring containing 0-3 heteroatoms;

Ring A is a 3-8 membered monocyclic, 8-12 membered bicyclic, or 10-14 membered tricyclic heterocyclyl which is either saturated or unsaturated and which contains 1-6 heteroatoms selected from O, N, and S;

Ring B is a 5-7 membered heterocyclyl containing 1-4 nitrogen atoms;

Ring C is a fused $C_{6-10}$ aryl or 5-10 membered heteroaryl ring;

Ring D is a 3-8 membered monocyclic, 8-12 membered bicyclic, or 10-14 membered tricyclic heterocyclyl which is either saturated or unsaturated and which contains 1-6 heteroatoms selected from O, N, and S;

Ring Z is a 6-membered aryl, 5-7 membered heteroaryl, $C_{3-7}$ cycloaliphatic or 5-7 membered heterocyclyl;

$R^5$ is H, halo, CN, $C_{1-12}$alkyl, NH$_2$, —NH($C_{1-12}$alkyl), —NH($C_{1-12}$alkyl)$_2$, OH, —O($C_{1-12}$alkyl), —O-(phenyl), $C_{1-12}$ haloalkyl, —O($C_{1-12}$haloalkyl), $C_{6-10}$aryl, —($C_{1-6}$alkyl)-$C_{6-10}$aryl, —C(O)($C_{1-12}$alkyl), —C(O)OH, —C(O)O($C_{1-12}$alkyl), —NHC(O)($C_{1-12}$alkyl), —N($C_{1-12}$alkyl)C(O)($C_{1-12}$alkyl), SO$_2$NH$_2$, —S(O)$_2$($C_{1-12}$alkyl), or —S(O)$_2$O($C_{1-12}$alkyl);

$R^6$ is H, $R^7$ or ($C_{1-12}$ alkyl)-(C=O)R$^7$;

$R^7$ is H, $C_{1-12}$ aliphatic, $C_{6-10}$ aryl, 5-10 membered heterocyclyl, 5-10 membered heteroaryl, $C_{3-10}$cycloaliphatic, —($C_{1-6}$alkyl)-$C_{6-10}$aryl, —($C_{1-6}$alkyl)-(5-10 membered heteroaryl), —($C_{1-6}$alkyl)-(5-10 membered heterocyclyl), —($C_{1-6}$alkyl)-benzo($C_{3-10}$cycloalkyl) or —($C_{1-6}$alkyl)-$C_{3-10}$cycloaliphatic;

or $R^6$ and $R^7$ taken together with the atom(s) to which they are attached form 3-8 membered monocyclic, 8-12 membered bicyclic, or 10-14 membered tricyclic ring which is either saturated or unsaturated and which contains 0-6 heteroatoms selected from O, N, and S;

$R^8$ is H, CF$_3$, halogen, NO$_2$, OCF$_3$, CN, OR$^7$, or R$^7$;

$R^9$ is H, CF$_3$, halogen, OCF$_3$, SR$^{11}$, CN, $C_{6-10}$aryl, $C_{5-10}$ heteroaryl, —O-(phenyl), or —S-(phenyl);

$R^{10}$ is $C_{1-6}$ alkyl optionally interrupted with up to 2 heteroatoms selected from O, N, or S;

$R^{11}$ and $R^{12}$ are each independently H or $C_{1-6}$ alkyl;

or $R^{11}$ and $R^{12}$, taken together with the atoms to which they are attached, form a 5-7 membered ring optionally containing up to 3 heteroatoms selected from O, N, or S;

$R^{13}$ is H, $C_{1-6}$ aliphatic, F$_2$, CN, $C_{6-10}$aryl, or $R^{13}$ is attached to Ar to form an unsaturated or partially saturated 5-6 membered ring having 0-2 heteroatoms which is fused to Ar;

$R^{14}$ is R, OR$^7$, or N(R$^7$)$_2$;

$R^{15}$ is R$^7$, NR$^7$, OR$^7$, or 2-t-butylphenyl;

$R^{16}$ is H, R$^7$, —($C_{1-6}$alkyl)-NR$^6$R$^7$, —($C_{1-6}$alkyl)-OR$^7$, —($C_{1-6}$alkyl)-NHCOR$^7$, —($C_{1-6}$alkyl)-NC(=NH)NH$_2$, —($C_{1-6}$alkyl)-NHCO$_2$R$^7$, —($C_{1-6}$alkyl)-SR$^7$, —($C_{1-6}$alkyl)-OR$^7$, —($C_{1-6}$alkyl)-cycloalkyl; or two R$^{16}$ taken together form a 3-6 membered carbocycle;

$R^{17}$ and $R^8$ are each independently H, $C_{1-6}$aliphatic, $C_{6-14}$aryl, or 5-14 membered heteroaryl; or $R^{17}$ and $R^{18}$, taken together with the atom(s) to which they are attached, form a 3-7 membered heterocyclyl with 1 heteroatom selected from O, N, or S;

$R^{19}$ is $C_{6-10}$aryl, —($C_{1-6}$alkyl)-$C_{6-10}$aryl, $C_{3-10}$cycloalkyl, or benzofused $C_{3-10}$cycloalkyl;

or $R^{19}$ and $AA_2$, together with the carbon atoms to which they are attached, form ring A.

In other embodiments of this invention, $R^1$ is selected from H, $R^4$, haloalkyl, CHN$_2$, CH$_2$Cl, CH$_2$F, —CH$_2$OR$^4$, —CH$_2$SR$^4$, —CH$_2$O(C=O)R$^4$, —CH$_2$OPO(R$^4$)$_2$, —CH$_2$OPO(OR$^4$)$_2$, CH$_2$NHR$^4$, or CH$_2$N(R$^4$)$_2$.

In yet other embodiments of this invention, $R^1$ is selected from H, $C_{1-6}$alkyl,

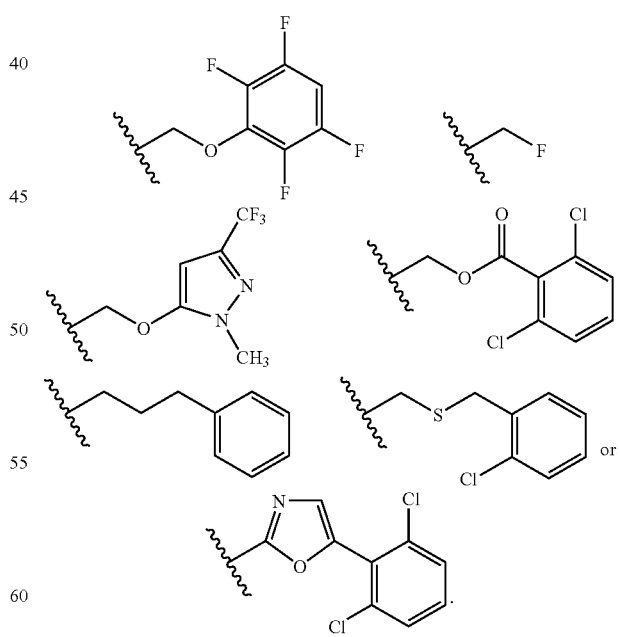

In other embodiments, $R^1$ is selected from —CH$_2$O-2,3,5,6-tetrafluorophenyl, —CH$_2$O-trifluorophenyl, CH$_2$F, or —CH$_2$O-tetrafluorophenyl.

In one embodiment, $R^1$ is

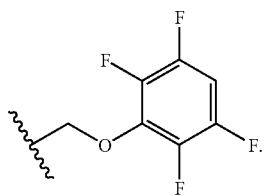

In another embodiment, R¹ is

In some embodiments, p is 0. In other embodiments, p is 1.

In some embodiments of this invention, T is —CO—, —CONH—, —C(O)O—, —C(O)C(O)— —SO₂—. In some embodiments T is —CO— or —SO₂—. In some embodiments, T is —CO—.

In some embodiments, R is H, $C_{1-12}$ aliphatic, $C_{6-10}$ aryl, 5-10 membered heteroaryl, or $C_{3-10}$ heterocyclyl. In some embodiments R is $C_{6-10}$ aryl or 5-10 membered heteroaryl. In some embodiments, R is naphthyl, phenyl, or isoquinolyl.

In certain embodiments of this invention, T is —CO— and R is $C_{6-10}$ aryl or 5-10 membered heteroaryl.

In some embodiments, T is —CO— and R is phenyl optionally substituted at the 3 and 5 position with halo or $C_{1-3}$alkyl and optionally substituted at the 4-position with NH₂, —NC(O)CH₃, OH, or OCH₃.

In some embodiments, AA, AA², and AA³ are each independently a group capable of fitting into the S2 sub-unit of a caspase. In some embodiments, AA, AA², and AA³ are each independently H or $C_{1-10}$aliphatic. In some embodiments AA, AA², and AA³ are each independently $C_{1-7}$ alkyl. In some embodiments, the $C_{1-7}$ alkyl is optionally substituted with halo, OH, SMe, —C(=O)OH, or phenyl.

In some embodiments, A² is O or S. In some embodiments A² is O. In other embodiments, A² is S.

According to another embodiment, ring A is selected from

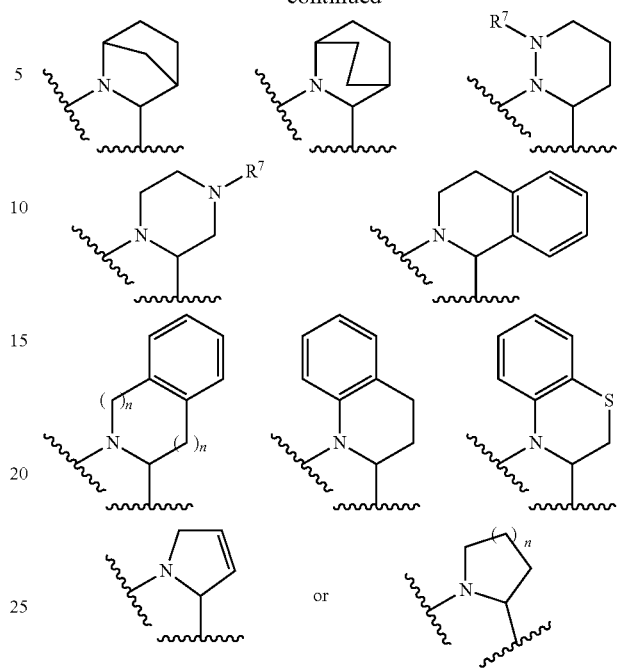

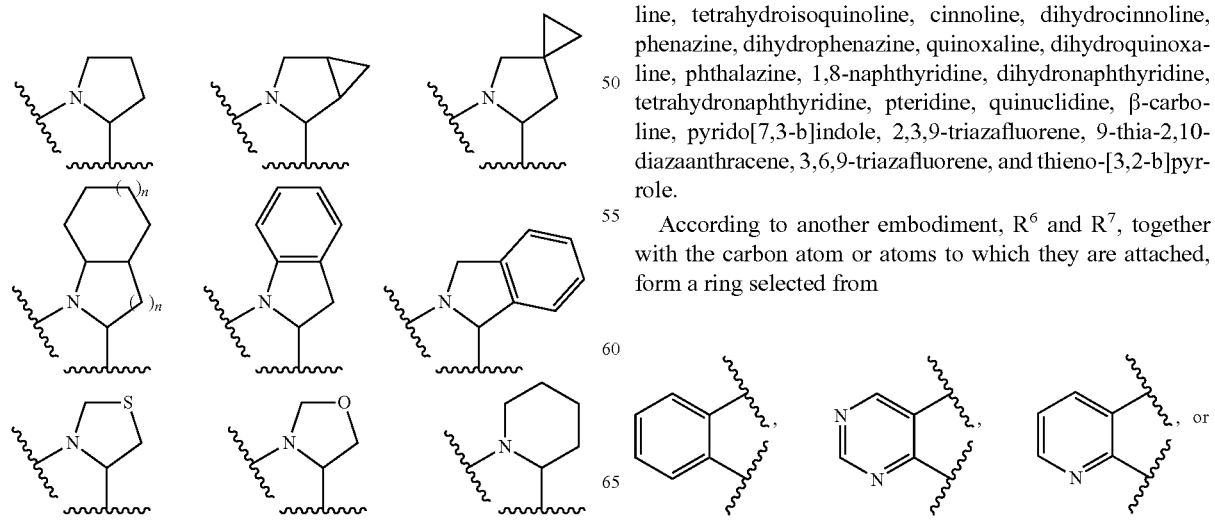

wherein n is 0-3.

In some embodiments ring A is substituted with 0-3 occurrences of J and 0-1 occurrences of J².

In some embodiments ring A is substituted with =O, halogen, $C_{1-4}$alkyl, or $C_{1-4}$alkoxy.

According to one embodiment, R⁶ and R⁷, together with the atom or atoms to which they are attached, form a ring selected from indole, isoindole, indoline, indazole, purine, dihydropyrimidine, benzimidazole, benzthiazole, imidazole, imidazoline, thiazole, pyrrole, pyrrolidone, pyrroline, pyrazole, pyrazoline, pyrazolidine, triazole, piperidine, morpholine, thiomorpholine, pyrazine, piperazine, carbazole, phenothiazine, phenoxazine, phenanthridine, dihydrophenanthridine, acridine, dihydroacridine, quinolizine, quinazoline, quinoline, isoquinoline, tetrahydroquinoline, tetrahydroisoquinoline, cinnoline, dihydrocinnoline, phenazine, dihydrophenazine, quinoxaline, dihydroquinoxaline, phthalazine, 1,8-naphthyridine, dihydronaphthyridine, tetrahydronaphthyridine, pteridine, quinuclidine, β-carboline, pyrido[7,3-b]indole, 2,3,9-triazafluorene, 9-thia-2,10-diazaanthracene, 3,6,9-triazafluorene, and thieno-[3,2-b]pyrrole.

According to another embodiment, R⁶ and R⁷, together with the carbon atom or atoms to which they are attached, form a ring selected from

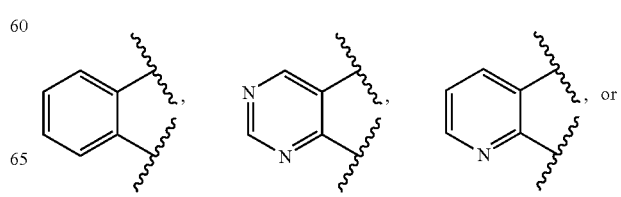

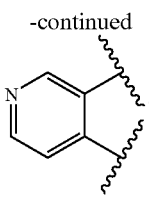

In some embodiments, the ring formed by $R^6$, $R^7$, and the atom or atoms to which they are attached, is substituted with 0-3 occurrences of J and 0-1 occurrences of $J^2$.

In some embodiments, $R^9$ is H, $CF_3$, halogen, $OCF_3$, $SR^{11}$, CN, $C_{6-10}$aryl, $C_{5-10}$ heteroaryl, —O-(phenyl), or —S-(phenyl); wherein said phenyl group is optionally substituted with 1-3 J groups, wherein J is halo, $CH_3$, $CF_3$, CN, $OCH_3$, $OCF_3$, or $N(R')_2$.

In some embodiments, Ar is a $C_{6-10}$aryl group. In some embodiments, Ar is a phenyl ring. In some embodiments Ar is optionally substituted with 0-3 occurrences of J and 0-1 occurrences of $J^2$. In some embodiments Ar is optionally substituted with 1-3 groups selected from halo, $CH_3$, $CF_3$, CN, $OCH_3$, $OCF_3$, and $NR^{11}R^{12}$.

According to one embodiment Z is

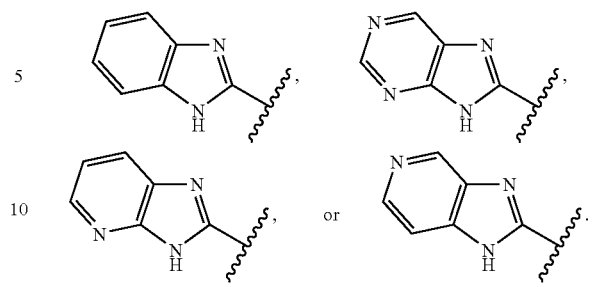

In some embodiments, Z is substituted with 0-3 occurrences of J and 0-1 occurrences of $J^2$.

In some embodiments, $G^1$, $G^2$, and $G^3$ are C. In some embodiments, Ring W contains two double bonds and forms a pyridone ring.

In some embodiments, the variables are as described in the compounds of Table 2.

In some embodiments the caspase inhibitor prodrug is selected from one depicted in Table 2:

TABLE 2

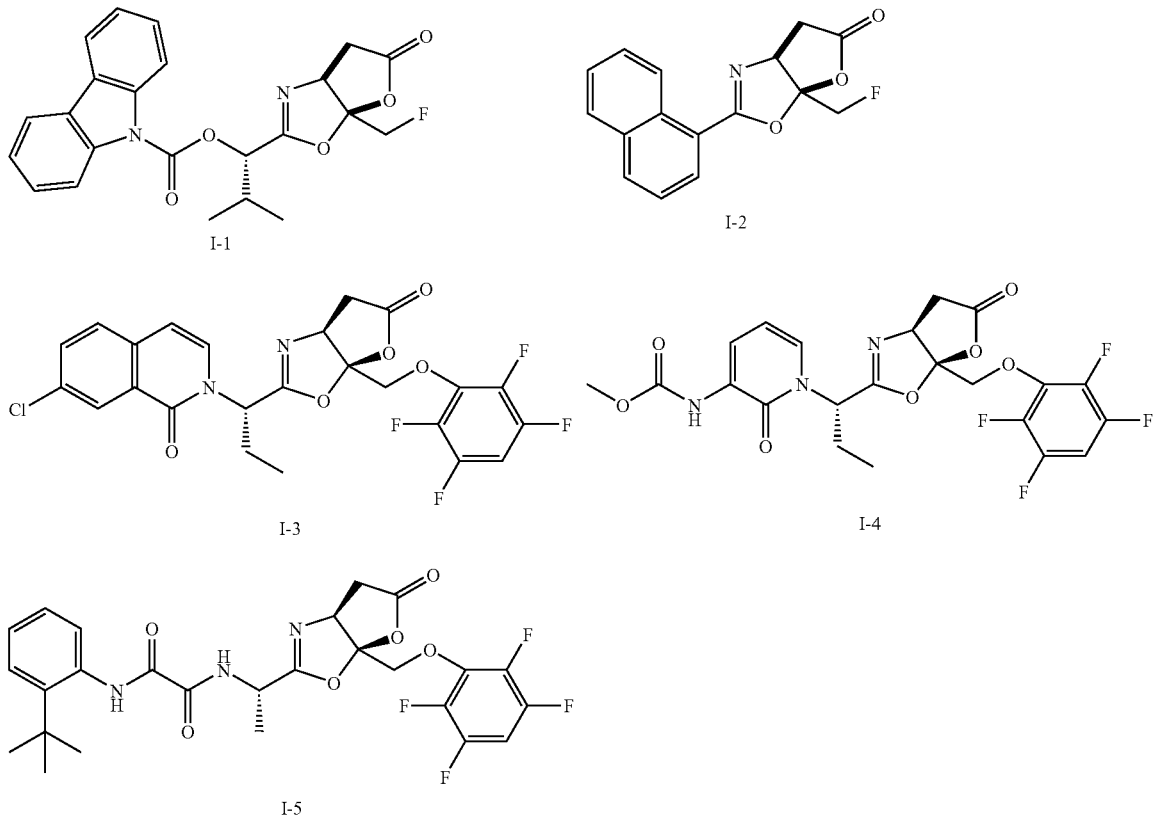

Although the structures above depict only one possible stereoisomer of the compound, this invention encompasses all possible syn stereoisomers of each compound. By way of example, compound I-2, as shown below on the left, represents one syn stereoisomer. The other syn isomer, shown on the right, is also part of this invention.

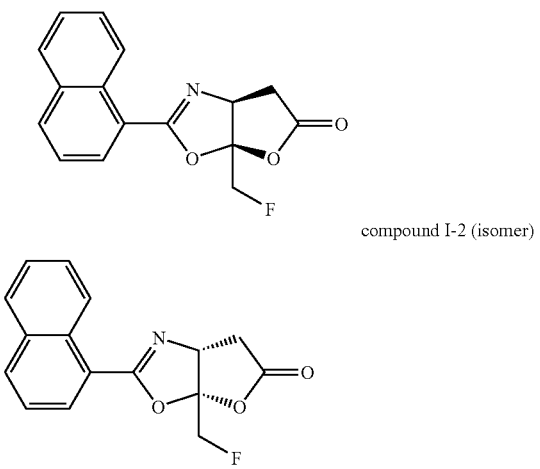

compound I-2 compound I-2 (isomer)

In certain embodiments, compounds of this invention, including compounds I-1 and I-2, are mixtures of the two syn isomers.

In other embodiments, compounds of this invention, including compounds I-3, I-4, and I-5, are enantiomerically pure syn isomers which have the conformation of the structures depicted in the table above.

According to another embodiment, the present invention provides a pharmaceutical composition comprising:

a) a compound of the invention, as defined herein, or a pharmaceutically acceptable salt thereof; and b) a pharmaceutically acceptable carrier, adjuvant or vehicle.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs. readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compounds and compositions are particularly useful in therapeutic applications relating to an IL-1 mediated disease, an apoptosis mediated disease, an inflammatory disease, an autoimmune disease, a destructive bone disorder, a proliferative disorder, an infectious disease (e.g., bacterial infections, preferably, eye infections), a degenerative disease, a disease associated with cell death, an excess dietary alcohol intake disease, a viral mediated disease, retinal disorders, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs. host disease, organ transplant rejection, organ apoptosis after burn injury, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, hemorrhagic shock, sepsis, septic shock, burns, Shigellosis, Alzheimer's disease, Parkinson's disease, Huntington's disease, Kennedy's disease, prion disease, cerebral ischemia, epilepsy, seizures, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, Japanese encephalitis, various forms of liver disease, renal disease, polycystic kidney disease, *H. pylori*-associated gastric and duodenal ulcer disease, HIV infection, tuberculosis, meningitis, toxic epidermal necrolysis, pemphigus, and autoinflammatory diseases (sometimes referred to as autoinflammatory fever syndromes) and related syndromes such as Muckle-Wells Syndrome (MWS), Familial Cold Urticaria (FCU), Familial Mediterranean Fever (FMF), Chronic Infantile Neurological Cutaneous and Articular Syndrome (CINCAS), a.k.a. Neonatal Onset Multisystem Inflammatory Disease (NOMID), TNFR1-Associated Periodic Syndrome (TRAPS), and Hyper-IgD periodic fever Syndrome (HIDS). The compounds and compositions are also useful in treating complications associated with coronary artery bypass grafts. The compounds and compositions are also useful for decreasing IGIF or IFN-γ production. The compounds and compositions are also useful in immunotherapy as a cancer treatment. It shall be understood that treating a disease includes lessening the severity of a disease, curing a disease, and keeping a disease stable or under control.

The compounds and compositions may. also be used in methods for preserving cells. These methods would be useful for preserving organs, particularly those intended for transplant, or blood products.

According to another embodiment, the compositions of this invention may further comprise another therapeutic agent (i.e., one or more additional agents). Such agents include, but are not limited to, thrombolytic agents such as tissue plasminogen activator and streptokinase. When an additional agent is used, the additional agent may be administered either as a separate dosage form or as part of a single dosage form with the compounds or compositions of this invention.

The amount of compound present in the compositions of this invention should be sufficient to cause a detectable decrease in the severity of the disease or in caspase activity and/or cell apoptosis, as measured by any of the assays known in the art.

Dosage levels of between about 0.01 and about 50 or about 100 mg/kg body weight per day, preferably between 0.5 and about 75 mg/kg body weight per day and most preferably between about 1 and about 25 or about 50 mg/kg body weight per day of the active ingredient compound are useful in a monotherapy.

Typically, a compound or composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of this invention and one or more additional therapeutic or prophylactic agents, both the compound and the additional agent should be present at dosage levels of between about 10% to about 100%, and more preferably between about 10% to about 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled practitioner will appreciate, lower or higher doses than those recited above may be required. It should be understood that a specific dosage and treatment regimens for any particular patient will depend upon a variety of factors, including the activity of the specific compound employed, the age, body weight, general health, sex, diet, time of administration, rate of excretion, drug combination, the severity and course of the particular disease, the patient's disposition to the disease being treated, and the judgment of the treating physician. The amount of active ingredients will also depend upon the particular compound and other therapeutic agent, if present, in the composition.

In a preferred embodiment, the invention provides a method of treating a patient, preferably a mammal, having one of the aforementioned diseases, comprising the step of administering to said patient a compound or a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

The compounds of this invention may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention and a carrier suitable for coating said implantable device. In still another aspect, the present invention includes an implantable device coated with a composition comprising a compound of the present invention and a carrier suitable for coating said implantable device.

Another aspect of the invention relates to inhibiting caspase activity in a biological sample, which method comprises contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of caspase activity in a biological sample is useful for a variety of purposes that are known to one of skill in the art. Examples of such purposes include, but are not limited to, blood transfusion, organ-transplantation, biological specimen storage, and biological assays.

The compounds of this invention are useful in methods for preserving cells, such as may be needed for an organ transplant or for preserving blood products. Similar uses for caspase inhibitors have been reported [Schierle et al., Nature Medicine, 5, 97 (1999)]. The method involves treating the cells or tissue to be preserved with a solution comprising the caspase inhibitor. The amount of caspase inhibitor needed will depend on the effectiveness of the inhibitor for the given cell type and the length of time required to preserve the cells from apoptotic cell death.

Without being bound by theory, applicants' cyclic acetal compounds are believed to be prodrugs. That is, the furo[3,2-d]oxazolin-5-one is cleaved in vivo or under appropriate conditions (e.g., in plasma) to provide an aspartic acid derivative that is an active compound.

In order that this invention be more fully understood, the following preparative and testing examples are set forth. These examples are for the purpose of illustration only and are not to be construed as limiting the scope of the invention in any way.

EXAMPLE 1

(S)-Carbazole-9-carboxylic acid 1-(3a-fluoromethyl-5-oxo-3a,5,6,6a-tetrahydro-furo[3,2-d]oxazol-2-yl)-2-methyl-propyl ester (I-1)

Method A

Trifluoroacetic anhydride (128 µL, 0.907 mmol, 2.0 Eq.) was added to a solution of (S)-carbazole-9-carboxylic acid 1-(1-carboxymethyl-3-fluoro-2-oxo-propylcarbamoyl)-2-methyl-propyl ester (200 mg, 0.752 mmol, 1.0 Eq.) in anhydrous dichloromethane (2 mL) under a nitrogen atmosphere at ambient temperature. After one hour, the reaction was diluted with anhydrous dichloromethane (10 mL) and tris-(2-aminoethyl)amine polystyrene resin (0.907 g, 3.07 mmol, 6.8 Eq.) was added and the reaction was stirred for a further one hour. The resin was removed by filtration and the filtrate concentrated in vacuo and triturated with dichloromethane and petroleum ether to give the title compound as a white solid (170 mg, 73%); $^1$H NMR (700 MHz, CDCl$_3$) δ 1.16-1.27 (6H, m), 2.79-2.55 (1H, m), 2.90 (1H, dd), 3.07 (1H, dd), 7.67-7.92 (3H, m), 5.61 (1H, dd), 7.72 (1H, t), 7.52 (1H, t), 8.02 (1H, d), 8.37 (1H, d); M+H 725.5.

EXAMPLE 2

3a-Fluoromethyl-2-naphthalen-1-yl-6,6a-dihydro-3aH-furo[3,2-d]oxazol-5-one (I-2)

Prepared from 5-fluoro-3-[(naphthalene-1-carbonyl)-amino]-7-oxo-pentanoic acid according to Method A (270 mg, 93%); White solid; $^1$H NMR (700 MHz, CDCl$_3$) δ 3.10 (1H, d), 3.20 (1H, dd), 7.85 (1H, dd), 7.97 (1H, dd), 5.18 (1H, d), 7.53-7.60 (2H, m), 7.67 (1H, t), 7.93 (1H, d), 8.06 (1H, d), 8.17 (1H, d), 9.17 (1H, d); $^{13}$C NMR (101 MHz, CDCl$_3$, proton decoupled) δ 35.7, 69.9, 80.7, 82.2, 125.0, 126.3, 126.9, 128.7, 129.2, 130.7, 131.3, 137.0, 137.1, 173.0; $^{19}$F NMR (376 MHz, CDCl$_3$, proton decoupled) δ −232.5; M+H 286.7.

EXAMPLE 3

(S,S,S)-7-Chloro-2-{1-[5-oxo-3a-(2,3,5,6-tetrafluoro-phenoxymethyl)-3a,5,6,6a-tetrahydro-furo[3,2-d]oxazol-2-yl]-propyl}-2H-isoquinolin-1-one (I-3)

Prepared from (S)-3-[2-(7-Chloro-1-oxo-1H-isoquinolin-2-yl)-butyrylamino]-7-oxo-5-(2,3,5,6-tetrafluoro-phenoxy)-pentanoic acid according to Method A (122 mg, 63%); White solid; IR (solid) 1795, 1659, 1616, 1586, 1509, 1785, 1093, 939, 827 cm⁻¹; ¹H NMR (700 MHz, CDCl₃) δ 0.98 (3H, t), 1.99-2.05 (1H, m), 2.25-2.30 (1H, m), 2.92 (1H, d), 3.15 (1H, dd), 7.59 (2H, dd), 7.99 (1H, d), 5.92-5.95 (1H, m), 6.66 (1H, d), 6.87-6.89 (1H, m), 7.01-7.03 (1H, m), 7.78 (1H, d), 7.62 (1H, dd), 8.72 (1H, brd d); ¹³C NMR (101 MHz, CDCl₃, proton-decoupled) δ 9.3, 23.6, 33.6, 51.8, 67.7, 72.0, 100.0 (t), 105.7, 111.7, 126.0, 126.7, 126.8, 127.0, 132.28, 132.7, 139.5 (dd), 175.3 (dd), 160.2, 163.9, 171.1; ¹⁹F NMR (376 MHz, CDCl₃, proton-decoupled) δ −170.21 (q), −170.37 (q), −158.10 (q), −158.60 (q); M+H 525.2, M−H 523.2.

EXAMPLE 4

(S,S,S)-(2-Oxo-1-{1-[5-oxo-3a-(2,3,5,6-tetrafluoro-phenoxymethyl)-3a,5,6,6a-tetrahydro-furo[3,2-d]oxazol-2-yl]-propyl}-1,2-dihydro-pyridin-3-yl)-carbamic acid methyl ester (I-4)

Prepared from (S,S)-3-[2-(3-methoxycarbonylamino-2-oxo-2H-pyridin-1-yl)-butyrylamino]-7-oxo-5-(2,3,5,6-tetrafluoro-phenoxy)-pentanoic acid according to Method A (38 mg, 80%); White solid; IR (solid) 1803, 1726, 1677, 1603, 1516, 1790, 1209, 1091, 937 cm⁻¹; ¹H NMR (700 MHz, CDCl₃) δ 0.96 (3H, t), 1.97-2.03 (1H, m), 2.22-2.03 (1H, m), 2.90 (1H, dd), 3.17 (1H, dd), 3.80 (3H, s), 7.59 (2H, dd), 7.97 (1H, d), 5.79-5.82 (1H, m), 6.31 (1H, t), 6.83-6.91 (2H, m), 7.79 (1H, brd s), 8.02 (1H, brd d); ¹³C NMR (101 MHz, CDCl₃, proton-decoupled) δ 10.7, 27.9, 37.7, 52.8, 57.3, 68.6, 73.3, 101.3 (t), 107.7, 112.6, 120.1, 125.7, 129.9, 157.7, 157.5, 167.7, 172.2; ¹⁹F NMR (376 MHz, CDCl₃, proton-decoupled) δ −138.95 (q), −157.33 (a); MHz 517.7, M−H 512.3

EXAMPLE 5

(S,S,S)-N-(2-tert-Butyl-phenyl)-N'-{1-[5-oxo-3a-(2,3,5,6-tetrafluoro-phenoxymethyl)-3a,5,6,6a-tetrahydro-furo[3,2-d]oxazol-2-yl]-ethyl}-oxalamide (I-5)

Prepared from (S,S)-3-{2-[(2-tert-Butyl-phenylaminooxalyl)-amino]-propionylamino}-7-oxo-5-(2,3,5,6-tetrafluoro-phenoxy)-pentanoic acid according to Method A (159 mg, 65%); White solid; IR (solid) 1808, 1675, 1518, 1793, 1779, 1100, 971, 760 cm⁻¹; ¹H NMR (700 MHz, CDCl₃) δ 1.77 (9H, s), 1.58 (3H, d), 2.90 (1H, brd dd), 3.12-3.19 (1H, m), 7.58-7.69 (2H, m), 7.80-7.86 (1H, m), 7.98 (1H, t), 6.87-6.93 (1H, m), 7.20 (1H, t), 7.28-7.32 (1H, m), 7.75 (1H, d), 8.03 (1H, d), 8.06 (1H, brd s), 9.57 (1H, brd d); ¹³C NMR (101 MHz, CDCl₃, proton-decoupled) δ 18.6, 18.7, 31.0, 37.7, 37.8, 77.7, 77.5, 68.3, 68.5, 73.2, 73.7, 101.3, 101.6, 113.1, 127.3, 126.5, 127.1, 127.7, 137.7, 160.3; ¹⁹F NMR (376 MHz, CDCl₃, proton-decoupled) δ −138.90 (dq), −157.22 (dq); M+H 552.5, M−H 550.7.

We claim:

1. A compound of formula I:

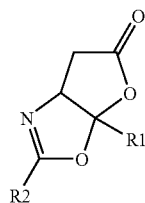

wherein $R^1$ is H, $C_{6-10}$ aryl, 5-10 membered heterocyclyl, 5-10 membered heteroaryl, $C_{3-10}$cycloaliphatic, —($C_{1-6}$alkyl)-$C_{6-10}$aryl, —($C_{1-6}$alkyl)-(5-10 membered heteroaryl), —($C_{1-6}$alkyl)-(5-10 membered heterocyclyl), or —($C_{1-6}$alkyl)-$C_{3-10}$cycloaliphatic; haloalkyl, $CHN_2$, $CH_2Cl$, $CH_2F$, —$CH_2OPO(R^4)_2$, —$CH_2OPO(OR^4)_2$, or —$C_{1-2}$alkyl-$R^3$-$R^4$;

$R^2$ is a $P_4$—$P_3$—$P_2$, $P_3$—$P_2$, or $P_2$ moiety of a caspase inhibitor; wherein the $P_3$—$P_2$ moiety of a caspase inhibitor is selected from the following scaffolds:

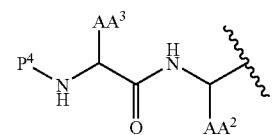

a

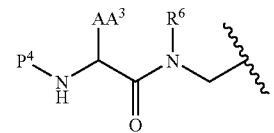

b

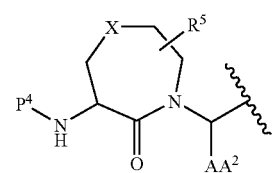

c

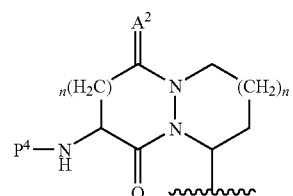

d

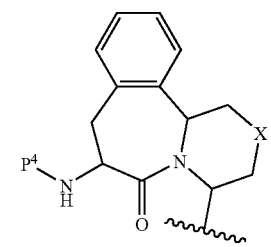

e

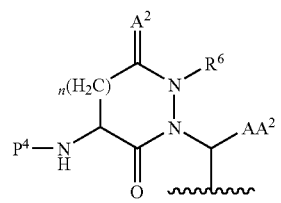

f

-continued
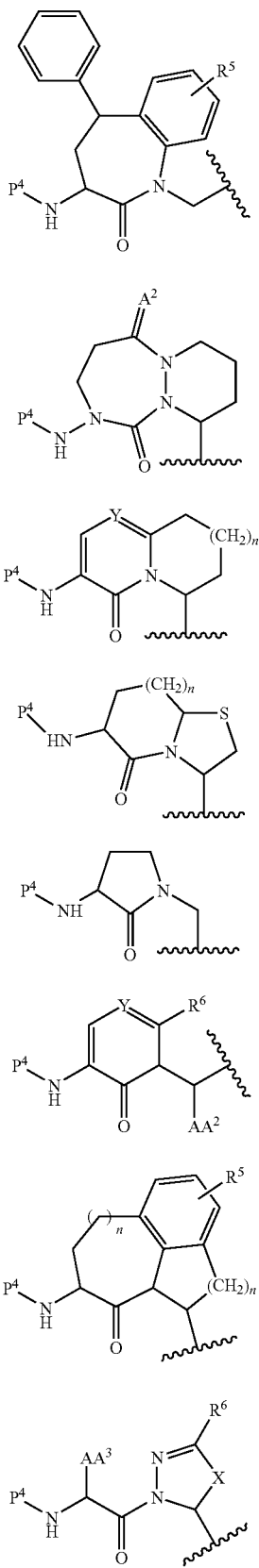
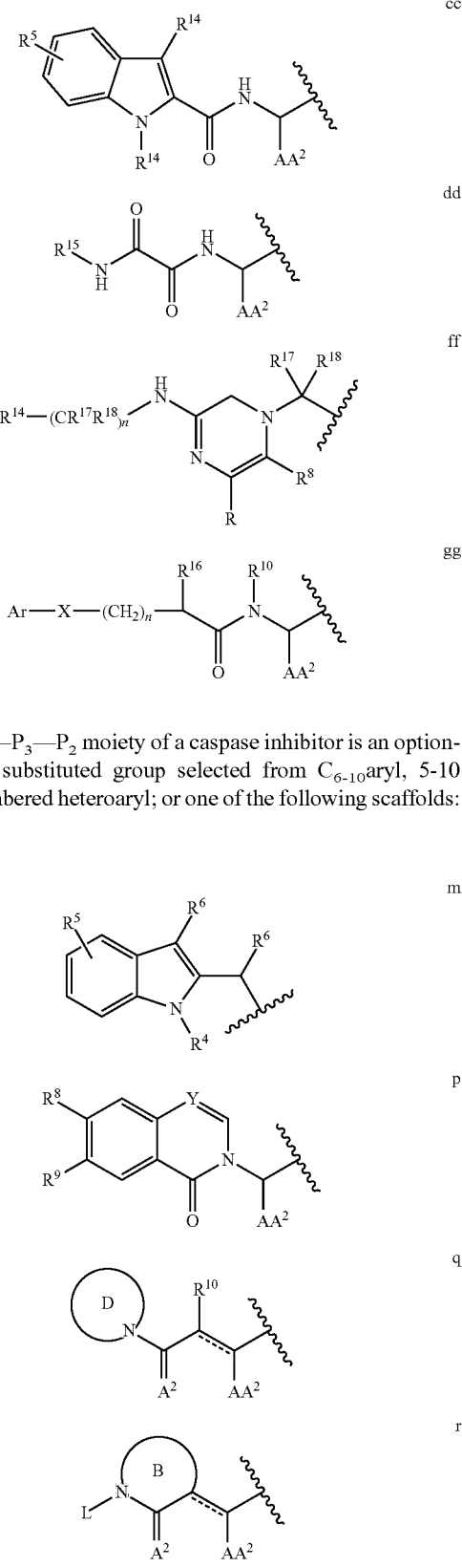
the P$_4$—P$_3$—P$_2$ moiety of a caspase inhibitor is an optionally substituted group selected from C$_{6-10}$aryl, 5-10 membered heteroaryl; or one of the following scaffolds:

-continued

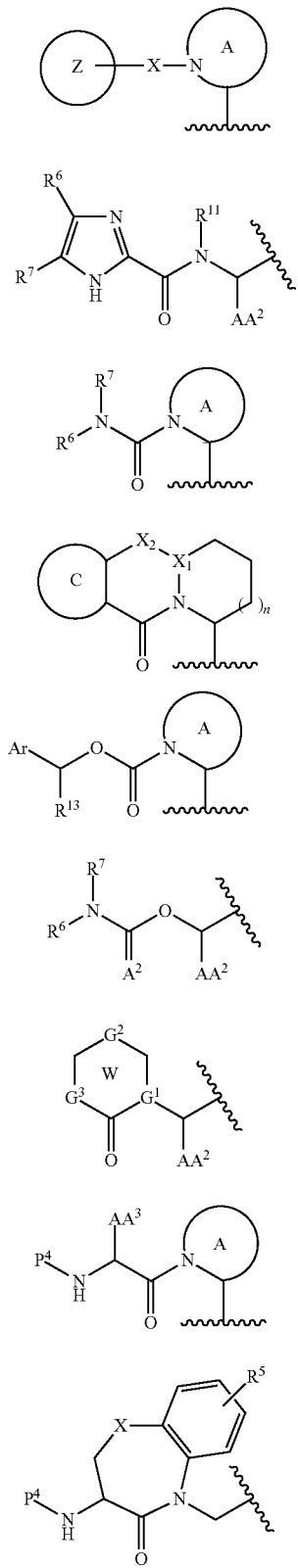

and the P₂ moiety of a caspase inhibitor is selected from the following scaffolds:

wherein
n is 0-3;
each $P^3$ and $P^4$ is independently -$(T)_p$-R;
T is —CO—, —C(O)O—, —C(O)C(O) O—, C(O)NR$^7$—, C(O)NR$^7$NR$^7$—, —C(O)C(O) NR$^7$—, —SO$_2$NR$^7$—, or —SO$_2$—;
p is 0 or 1;
R is H, $C_{1-12}$ aliphatic, $C_{6-10}$ aryl, 5-10 membered heterocyclyl, 5-10 membered heteroaryl, $C_{3-10}$cycloaliphatic, —($C_{1-6}$alkyl)-$C_{6-10}$aryl, —($C_{1-6}$alkyl)-(5-10 membered heteroaryl), —($C_{1-6}$alkyl)-(5-10 membered heterocyclyl), —($C_{1-6}$alkyl)-benzo($C_{3-10}$cycloalkyl) or —($C_{1-6}$alkyl)-$C_{3-10}$cycloaliphatic;
each AA, AA$^2$, and AA$^3$ is independently an amino acid side chain;
X is —NH—, —O—, —S—, —SO—, —SO$_2$—, —CHF—, —CF$_2$—, —C(R$^{11}$)$_2$—, —C=O—, or —C=NOR$^{11}$—;
$X_2$-$X_1$ is —N(R$^{11}$)—C(R$^{11}$)—, —C(R$^{11}$)$_2$—C(R$^{11}$)—, —C(R$^{11}$)$_2$—N—, —N=C—, —C(R$^{11}$)=N—, —C(R$^{11}$)=C—, —C(=O)—N—, or —C(=O)—C(R$^{11}$)—;
A$^2$ is O, S, or H$_2$;
Y is N or CR$^8$;
Ar is optionally substituted $C_{6-10}$ aryl or optionally substituted 5-10 membered heteroaryl;
L is R$^7$, (CH$_2$)$_n$R$^7$, COR$^7$, CO$_2$R$^7$, SO$_2$R$^7$, CON(R$^7$)$_2$, or SO$_2$N(R$^7$)$_2$;
G$^1$ and G$^3$ are independently selected from N or C;
G$^2$ is a valence bond, O, S, N, or C;
Ring W contains 0-2 double bonds and is optionally fused to a saturated or unsaturated 5-7 membered ring containing 0-3 heteroatoms;
Ring A is a 3-8 membered monocyclic, 8-12 membered bicyclic, or 10-14 membered tricyclic heterocyclyl which is either saturated or unsaturated and which contains 1-6 heteroatoms selected from O, N, and S;
Ring B is a 5-7 membered heterocyclyl containing 1-4 nitrogen atoms;
Ring C is a fused $C_{6-10}$ aryl or 5-10 membered heteroaryl ring;
Ring D is a 3-8 membered monocyclic, 8-12 membered bicyclic, or 10-14 membered tricyclic heterocyclyl which is either saturated or unsaturated and which contains 1-6 heteroatoms selected from O, N, and S;
Ring Z is a 6-membered aryl, 5-7 membered heteroaryl, $C_{3-7}$ cycloaliphatic, or 5-7 membered heterocyclyl;
R$^5$ is H, halo, CN, $C_{1-12}$alkyl, NH$_2$, —NH($C_{1-12}$alkyl), —NH($C_{1-12}$alkyl)$_2$, OH, —O($C_{1-12}$alkyl), —O-(phenyl), $C_{1-12}$ haloalkyl, —O($C_{1-12}$haloalkyl), $C_{6-10}$aryl, —($C_{1-6}$alkyl)-$C_{6-10}$aryl, —C(O)($C_{1-12}$alkyl), —C(O) OH, —C(O)O($C_{1-12}$alkyl), —NHC(O)($C_{1-12}$alkyl), —N($C_{1-12}$alkyl)C(O)($C_{1-12}$alkyl), SO$_2$NH$_2$, —S(O)$_2$($C_{1-12}$alkyl), or —S(O)$_2$O($C_{1-12}$alkyl);
R$^6$ is H, R$^7$ or ($C_{1-12}$ alkyl)-(C=O)R$^7$;
R$^7$ is H, $C_{1-12}$ aliphatic, $C_{6-10}$ aryl, 5-10 membered heterocyclyl, 5-10 membered heteroaryl, $C_{3-10}$cycloaliphatic, —(C$_{1-6}$alkyl)-C$_{6-10}$aryl, —(C$_{1-6}$alkyl)-(5-10 membered heteroaryl), —(C$_{1-6}$alkyl)-(5-10 membered heterocyclyl), —(C$_{1-6}$alkyl)-benzo(C$_{3-10}$cycloalkyl) or —(C$_{1-6}$alkyl)-C$_{3-10}$cycloaliphatic;

or R$^6$ and R$^7$ taken together with the atom(s) to which they are attached form 3-8 membered monocyclic, 8-12 membered bicyclic, or 10-14 membered tricyclic ring which is either saturated or unsaturated and which contains 0-6 heteroatoms selected from O, N, and S;

R$^8$ is H, CF$_3$, halogen, NO$_2$, OCF$_3$, CN, OR$^7$, or R$^7$;

R$^9$ is H, CF$_3$, halogen, OCF$_3$, SR$^{11}$, CN, C$_{6-10}$aryl, C$_5$-10 heteroaryl, —O—(phenyl), or —S—(phenyl);

R$^{10}$ is C$_{1-6}$ alkyl optionally interrupted with up to 2 heteroatoms selected from O, N, or S;

R$^{11}$ and R$^{12}$ are each independently H or C$_{1-6}$ alkyl;

or R$^{11}$ and R$^{12}$, taken together with the atoms to which they are attached, form a 5-7 membered ring optionally containing up to 3 heteroatoms selected from O, N, or S;

R$^{13}$ is H, C$_{1-6}$ aliphatic, F$_2$, CN, C$_{6-10}$aryl, or R$^{13}$ is attached to Ar to form an unsaturated or partially saturated 5-6 membered ring having 0-2 heteroatoms which is fused to Ar;

R$^{14}$ is R, OR$^7$, or N(R$^7$)$_2$;

R$^{15}$ is R$^7$, NR$^7$, OR$^7$, or 2-t-butylphenyl;

R$^{16}$ is H, R$^7$, —(C$_{1-6}$alkyl)-NR$^6$R$^7$, —(C$_{1-6}$alkyl)-OR$^7$, —(C$_{1-6}$alkyl)-NHCOR$^7$, —(C$_{1-6}$alkyl)-NC(=NH)NH$_2$, —(C$_{1-6}$alkyl)-NHCO$_2$R$^7$, —(C$_{1-6}$alkyl)-SR$^7$, —(C$_{1-6}$alkyl)-OR$^7$, —(C$_{1-6}$alkyl)-cycloalkyl; or two R$^{16}$ taken together form a 3-6 membered carbocycle;

R$^{17}$ and R$^{18}$ are each independently H, C$_{1-6}$aliphatic, C$_{6-14}$aryl, or 5-14 membered heteroaryl; or R$^{17}$ and R$^{18}$, taken together with the atom(s) to which they are attached, form a 3-7 membered heterocyclyl with 1 heteroatom selected from O, N, or S;

R$^{19}$ is C$_{6-10}$aryl, —(C$_{1-6}$alkyl)-C$_{6-10}$aryl, C$_{3-10}$cycloalkyl, or benzofused C$_{3-10}$cycloalkyl;

or R$^{19}$ and AA$_2$, together with the carbon atoms to which they are attached, form ring A;

R$^3$ is —O—, —NH—, —NR$^4$—, —S—, or —O(C=O)—;

R$^4$ is C$_{1-12}$ aliphatic, C$_{6-10}$ aryl, 5-10 membered heterocyclyl, 5-10 membered heteroaryl, C$_{3-10}$cycloaliphatic, —(C$_{1-6}$alkyl)-C$_{6-10}$aryl, —(C$_{1-6}$alkyl)-(5-10 membered heteroaryl), —(C$_{1-6}$alkyl)-(5-10 membered heterocyclyl), or —(C$_{1-6}$alkyl)-C$_{3-10}$cycloaliphatic;

wherein said R$^4$ group is optionally substituted with 0-5 J and 0-2 J$^2$;

or two R$^4$ groups, together with the atom to which they are attached, form a 3-8 membered monocyclic or 8-12 membered bicyclic ring optionally substituted with 0-5 J and 0-2 J$^2$;

J is halogen, —OR', —NO$_2$, —CN, —CF$_3$, —OCF$_3$, —R', 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)C(O)OR', —C(O)C(O)N(R')$_2$, —C(O)CH$_2$C(O)R', —C(S)R', —C(S)OR', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NR')N(R')$_2$, —C(O)N(OR')R', —C(=NOR')R', —OP(O)(OR')$_2$, —P(O)(R')$_2$, —P(O)(OR')$_2$, or —P(O)(H)(OR');

J$^2$ is =NR', =N(OR'), =O, or =S;

R' is H, C$_{1-12}$ aliphatic, C$_{6-10}$ aryl, 5-10 membered heterocyclyl, 5-10 membered heteroaryl, C$_{3-10}$cycloaliphatic, —(C$_{1-6}$alkyl)-C$_{6-10}$aryl, —(C$_{1-6}$alkyl)-(5-10 membered heteroaryl), —(C$_{1-6}$alkyl)-(5-10 membered heterocyclyl), or —(C$_{1-6}$alkyl)-C$_{3-10}$cycloaliphatic;

each R' is independently and optionally substituted with 0-5 occurrences of H, C$_{1-6}$alkyl, CF$_3$, halogen, NO$_2$, OCF$_3$, CN, OH, O(C$_{1-6}$alkyl), NH$_2$, N(C$_{1-6}$alkyl), N(C$_{1-6}$alkyl)$_2$, C(=O)CH$_3$, or C$_{1-6}$alkyl optionally interrupted 1 time with a heteroatom selected from O, N, and S; wherein each C$_{1-6}$alkyl is unsubstituted;

unless otherwise indicated, any group with suitable valence is optionally substituted with 0-5 J and 0-2 J$^2$.

2. The compound according to claim 1, wherein R$^1$ is selected from H, C$_{6-10}$ aryl, 5-10 membered heterocyclyl, 5-10 membered heteroaryl, C$_{3-10}$cycloaliphatic, —(C$_{1-6}$alkyl)-C$_{6-10}$aryl, —(C$_{1-6}$alkyl)-(5-10 membered heteroaryl), —(C$_{1-6}$alkyl)-(5-10 membered heterocyclyl), or —(C$_{1-6}$alkyl)-C$_{3-10}$cycloaliphatic; haloalkyl, CHN$_2$, CH$_2$Cl, CH$_2$F, —CH$_2$OR$^4$, —CH$_2$SR$^4$, —CH$_2$O(C=O)R$^4$, —CH$_2$OPO(R$^4$)$_2$, —CH$_2$OPO(OR$^4$)$_2$, CH$_2$NHR$^4$, and CH$_2$N(R$^4$)$_2$.

3. The compound according to claim 1, wherein R$^1$ is selected from H,

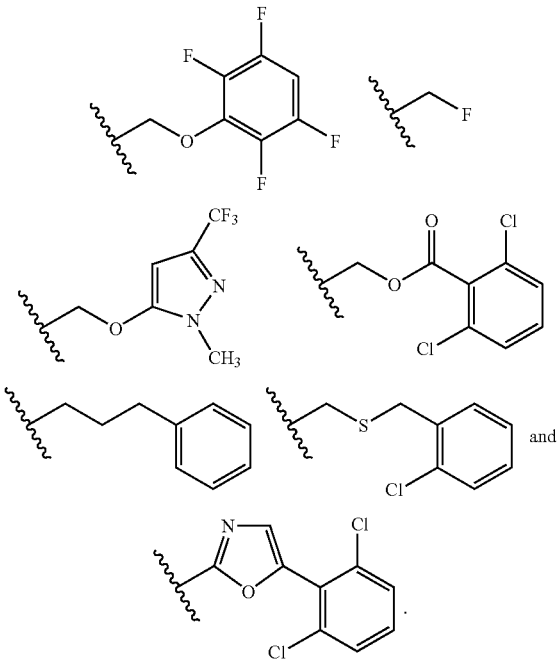

4. The compound according to claim 3, wherein R$^1$ is

5. The compound according to claim 3, wherein R$^1$ is

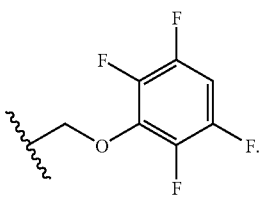

6. The compound according to claim 1, wherein
T is —CO— or —SO$_2$—; and
R is H, C$_{1-12}$ aliphatic, C$_{6-10}$aryl, 5-10 membered heteroaryl, or C$_{3-10}$ heterocyclyl.

7. The compound according to claim 6, wherein T is —CO— and R is optionally substituted phenyl.

8. The compound according to claim 1, wherein AA, AA$^2$, and AA$^3$ are each independently C$_{1-7}$ alkyl.

9. The compound according to claim 8, wherein the C$_{1-7}$ alkyl is optionally substituted with halo, OH, SMe, —C(=O)OH, or phenyl.

10. The compound according to claim 1, wherein A$^2$ is O.

11. The compound according to claim 1, wherein G$^1$, G$^2$, and G$^3$ are C and ring W is a pyridone ring.

12. The compound according to claim 1, wherein ring A is:

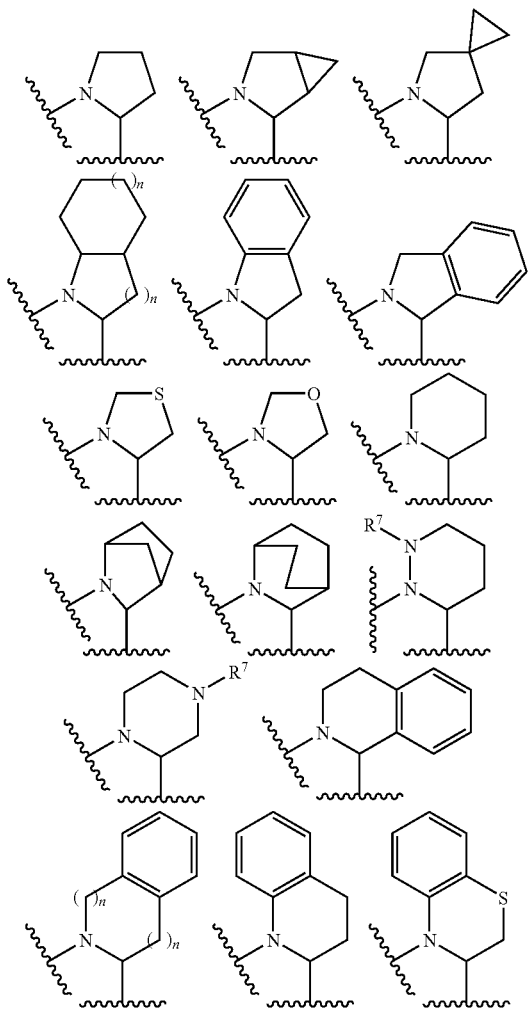

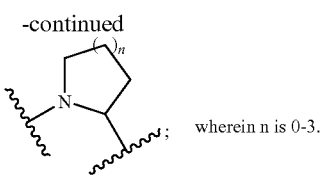

wherein n is 0-3.

13. The compound according to claim 1, wherein Z is an optionally substituted group selected from

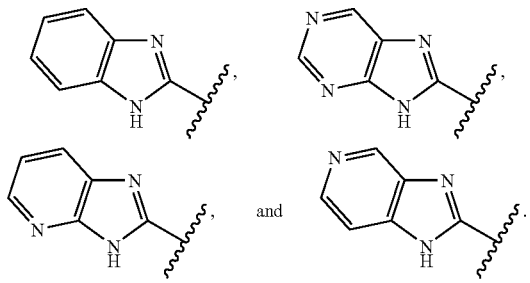

14. The compound according to claim 1, wherein R$^6$ and R$^7$, together with the atom or atoms to which they are attached, form a ring selected from indole, isoindole, indoline, indazole, purine, dihydropyrimidine, benzimidazole, benzothiazole, imidazole, imidazoline, thiazole, pyrrole, pyrrolidone, pyrroline, pyrazole, pyrazoline, pyrazolidine, triazole, piperidine, morpholine, thiomorpholine, pyrazine, piperazine, carbazole, phenothiazine, phenoxazine, phenanthridine, dihydrophenanthridine, acridine, dihydroacridine, quinolizine, quinazoline, quinoline, isoquinoline, tetrahydroquinoline, tetrahydroisoquinoline, cinnoline, dihydrocinnoline, phenazine, dihydrophenazine, quinoxaline, dihydroquinoxaline, phthalazine, 1,8-naphthyridine, dihydronaphthyridine, tetrahydronaphthyridine, pteridine, quinuclidine, β-carboline, pyrido[7,3-b]indole, 2,3,9-triazafluorene, 9-thia-2,10-diazaanthracene, 3,6,9-triazafluorene, and thieno-[3,2-b]pyrrole.

15. The compound according to claim 1, wherein R$^6$ and R$^7$, together with the carbon atom or atoms to which they are attached, form a ring selected from

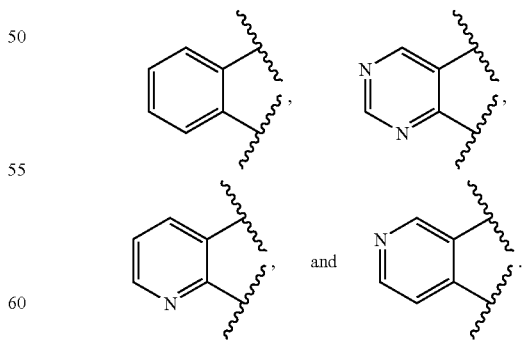

16. The compound according to claim 1, wherein Ar is a phenyl ring optionally substituted with 1-3 groups selected from halo, CH$_3$, CF$_3$, CN, OCH$_3$, OCF$_3$, and NR$^{11}$R$^{12}$.

17. The compound of claim 1, selected from the following:

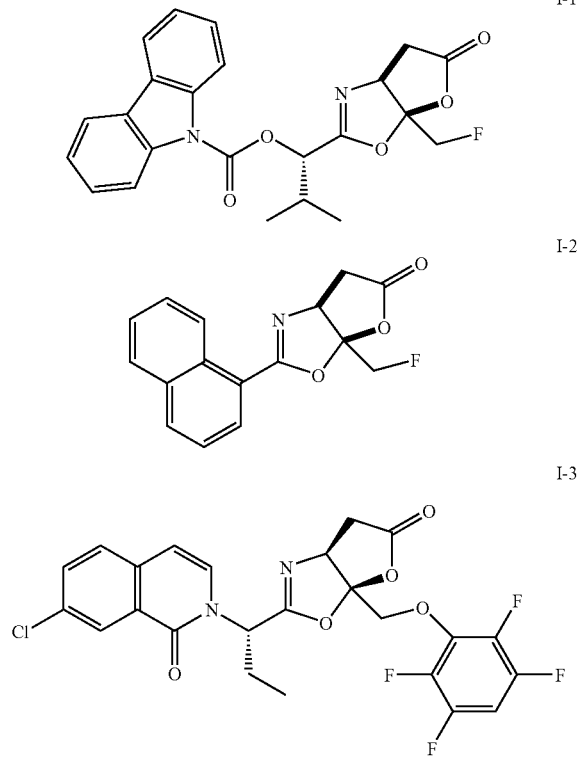
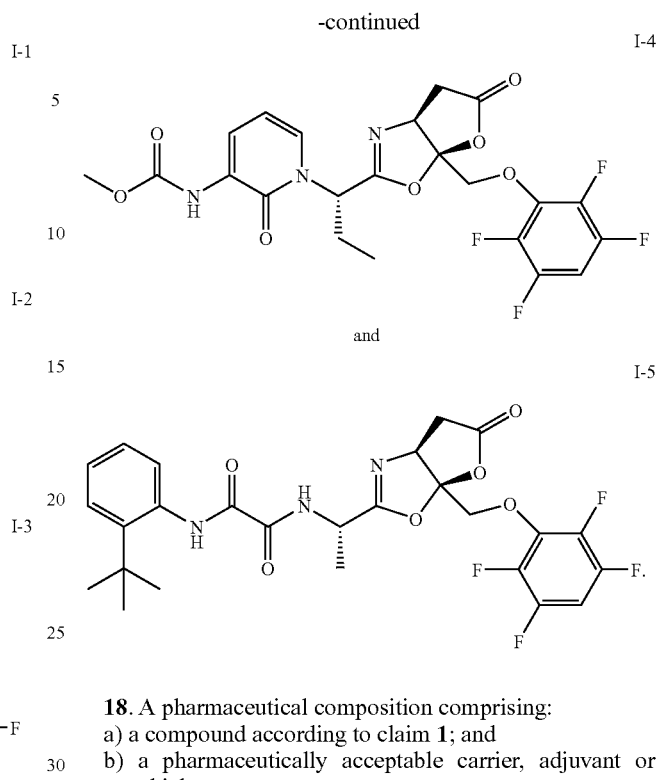
18. A pharmaceutical composition comprising:
a) a compound according to claim 1; and
b) a pharmaceutically acceptable carrier, adjuvant or vehicle.
* * * * *